United States Patent [19]

Fontana et al.

[11] Patent Number: 4,827,002

[45] Date of Patent: May 2, 1989

[54] PROCESS FOR PREPARING ADDUCTS OF ALCOHOLS, ETHERS AND ESTERS WITH 1,2-DICHLORODIFLUOROETHYLENE

[75] Inventors: Alberto Fontana; Silvana Modena; Giovanni Moggi, all of Milan, Italy

[73] Assignee: Montefluos S.P.A., Milan, Italy

[21] Appl. No.: 739,909

[22] Filed: May 31, 1985

[30] Foreign Application Priority Data

Jun. 1, 1984 [IT] Italy ................................. 21216 A/84

[51] Int. Cl.$^4$ ..................... C07D 321/00; C07C 41/00
[52] U.S. Cl. .................................. 549/346; 549/347; 549/380; 549/455; 549/504; 560/266; 568/184; 568/842
[58] Field of Search ................ 568/684, 842; 560/266; 549/380, 504, 346, 347, 455; 204/158 R, 158 HA

[56] References Cited

U.S. PATENT DOCUMENTS 2,559,628 7/1951 Joyce, Jr. ............................ 568/842

OTHER PUBLICATIONS

Muramatsu, J. Org. Chem., vol. 27, 2325 (1962).
Muramatsu, J. Org. Chem., vol. 29, 2220 (1964).

*Primary Examiner*—Anton H. Sutto

*Attorney, Agent, or Firm*—Stevens, Davis, Miller & Mosher

[57] ABSTRACT

There are prepared compounds of general formula:

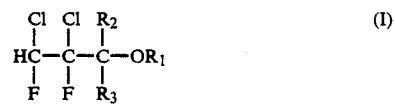

wherein: $R_1 = H$, or alkyl or acyl containing from 1 to 10 carbon atoms, $R_2$, $R_3$, like or unlike each other, may be H, or an alkyl containing from 1 to 10 carbon atoms and where $R_1$ and $R_2$ may form, together, an alkylene group containing from 2 to 10 carbon atoms, and optionally including up to 2 oxygen atoms in the chain, by means of addition reaction induced by radicalic starters of 1,2-dichlorodifluoroethylene to alcohols, ethers or esters of general formula:

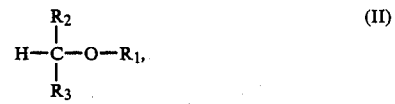

wherein: $R_1$, $R_2$, $R_3$ are defined as above.

3 Claims, No Drawings

PROCESS FOR PREPARING ADDUCTS OF ALCOHOLS, ETHERS AND ESTERS WITH 1,2-DICHLORODIFLUOROETHYLENE

BACKGROUND OF THE INVENTION

It is known from the article by H. Muramatsu in J. Org. Chem. 27, 2325 (1962) and 29, 2220 (1964) to prepare adducts of halogenated olefins to alcohols, ethers and esters by operating in the presence of gamma rays.

The necessity of using such radiation makes said method off little use in the industrial practice.

THE PRESENT INVENTION

We have now surprisingly found that the above-said compounds are advantageously preparable by addition reaction of 1,2-dichlorodifluoroethylene to alcohols, ethers and esters having at least a hydrogen atom on the carbon in alpha position with respect to the oxygen atom, by operating in the presence of radicalic starters.

The alcohols, ethers and esters defined hereinbefore are generally comprised in general formula:

wherein $R_1$, $R_2$, $R_3$ are the same as defined hereinbefore.

Thus, it is the object of the present invention to provide a process for preparing the compounds having the abovementioned general formula and consisting in reacting 1,2-di-chlorodifluoroethylene with at least a compound comprised in the above-cited general formula (II), in the presence of radicalic starters.

Peroxides are preferably employed as radicalic starters in the reaction. Among these, di-tert.butylperoxide has proved to be particularly suitable.

The preparation of the compounds of formula (I) according to the present invention is accomplished in practice by reacting 1,2-dichlorodifluoroethylene with at least a compound of formula (II), in the presence of peroxides, in an autoclave at a temperature in the range of 0° to 200° C. (chosen as a function of the peroxide utilized), employing a molar ratio between olefin and such compound comprised between 100:1 and 1:100 (but preferably between 1:3 and 1:100) and a molar concentration of the peroxide with respect to the olefin comprised between 0.1 and 100%, but preferably between 20 and 60%.

Summarizing, the present process for preparing compounds having general formula I:

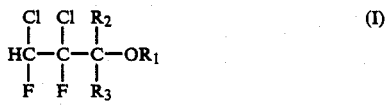

wherein:
$R_1$ is H or alkyl or acyl containing from 1 to 10 carbon atoms;
$R_2$, $R_3$, like or unlike each other, may be H, or an alkyl containing from 1 to 10 carbon atoms and where $R_1$ and $R_2$ may also form, together, an alkylene group containing from 2 to 10 carbon atoms, and optionally comprising up to 2 carbon atoms in the chain, by means of addition reaction induced by a peroxide as a radicalic starter of 1,2-dichloro-difluoroethylene to alcohols, ethers and esters of the general formula (II), wherein $R_1$, $R_2$, $R_3$ are the same as in formula (I), the molar ratio between olefin and ester, ether or alcohol being from 100:1 to 1:100, and the molar concentration of peroxide with respect to the olefin being from 0.1 to 100%.

The reaction times may vary from 5 minutes to 50 hours, but they are generally comprised between 1 hour and 6 hours.

The process forming the object of the present invention is easily transferable to industrial plants, contrary to the ones already described in literature and relating to the use of gamma rays. P For a better understanding of the present invention and for the embodiment thereof a few non-limitative examples are given hereinafter.

EXAMPLE 1

Preparation of 2,3-dichloro-2,3-difluoro-1-propanol.

40 g of 1,2-dichlorodifluoroethylene, 87 g of methanol and 22 g of di-tert.butylperoxide were charged into a 500-ml AISI 316 autoclave. The temperature was brought to 150° C. and stirring was conducted during 5 hours.

The autoclave was cooled down to 0° C., the evolved gases were vented-off and the reaction mixture was rectified, thus obtaining 5 g of 2,3-dichloro-2,3-difluoro-1-propanol; the unreacted olefin was recovered. The product had a boiling point of 75° at 40 mm of Hg and was identified by means of gas-mass analysis, N.M.R. spectrometry and centesimal analysis.

EXAMPLE 2

Preparation of 3,4-dichloro-3,4-difluoro-2-butanol.

The synthesis was conducted by operating according to the modalities of example 1, using 124 g of absolute ethanol.

8 g of 3,4-dichloro-3,4-difluoro-2-butanol were obtained; the unreacted olefin was recovered by means of rectification. The product exhibited a boiling point of 65° at 20 mm of Hg and was identified by means of gas-mass analysis, N.M.R. spectrometry and centesimal analysis.

EXAMPLE 3

Preparation of 2-methyl-3,4-dichloro-3,4-difluoro-2-butanol.

The synthesis was conducted by operating according to the modalities of example 1, utilizing 162 g of 2-propanol. 17 g of 2-methyl-3,4-dichloro-3,4-difluoro-2-butanol were obtained; the unreacted olefin was recovered by means of rectification. The product had a boiling point of 74° at 40 mm of Hg and was identified by means of gas-mass analysis, N.M.R. spectrometry and centesimal analysis.

EXAMPLE 4

Preparation of 1,2-dichloro-1,2-difluoro-3-pentanol.

The synthesis was conducted by operating according to the modalities of example 1, using 162 g of 1-propanol. There were obtained 10 g of 1,2-dichloro-1,2-difluoro-3-pentanol; the unreacted olefin was recovered by means of rectification. The product exhibited a boiling point of 80° at 20 mm Hg and was identified by means of gas-mass analysis, N.M.R. spectrometry and centesimal analysis.

EXAMPLE 5

Preparation of (2,3-dichloro-2,3-difluoropropyl) acetate.

The synthesis was conducted by operating according to the modalities of example 1, employing 200 g of methyl acetate. Obtained were 8.6 g of (2,3-dichloro-2,3-difluoropropyl) acetate; the unreacted olefin was recovered by means of rectification. The product exhibited a boiling point of 74° at 45 mm Hg and was identified by means of gas-mass analysis, N.M.R. spectrometry and centesimal analysis.

EXAMPLE 6

Preparation of (1-methyl-2,3-dichoro-2,3difluoropropyl)acetate.

The synthesis was conducted by operating according to the modalities of example 1, employing 238 g of ethyl acetate. There were obtained 13 g of (1-methyl-2,3-dichloro-2,3-difluoropropyl); the unreacted olefin was recovered by means of rectification. The product exhibited a boiling point of 95° at 40 mm Hg and was identified by means of gas-mass analysis, N.M.R. spectrometry and centesimal analysis.

EXAMPLE 7

Preparation of (1,1-dimethyl-2,3-dichloro-2,3-difluoropropyl) acetate.

The synthesis was conducted by operating according to the modalities of example 1, utilizing 275 g of isopropyl acetate. There were obtained 16 g of (1,1-dimethyl-2,3-dichloro-2,3-difluoropropyl) acetate; the unreacted olefin was recovered by means of rectification. The product had a boiling point of 86° at 20 mm Hg and was identified by means of gas-mass analysis, N.M.R. spectrometry and centesimal analysis.

EXAMPLE 8

Preparation of 1-methyl-2,3-dichloro-2,3-difluoropropyl-ethylether.

The synthesis was conducted by operating according to the modalities of example 1, using 200 g of diethyl ether. There were obtained 5 g of 1-methyl-2,3-dichloro-2,3-difluoropropyl-ethylether (A) and 20 g of (1-methyl-2,3-dichloro-2,3-difluoropropyl) ether (B). Product (A) had a boiling point of 68° at 50 mm Hg, while product (B) exhibited a boiling point of 134° at 20 mm Hg. Both products were identified by means of N.M.R. spectrometry and centesimal analysis.

EXAMPLE 9

Preparation of 2-(1',2'-dichloro-1',2'-difluoroethyl) tetrahydrofuran.

The synthesis was conducted by operating according to the modalities pf example 1, using 195 g of tetrahydrofuran.

There were obtained 18.4 g of 2-(1',2'-dichloro-1',2'-difluoroethyl)-tetrahydrofuran; the unreacted olefin was recovered by rectification. The product exhibited a boiling point of 110° at 60 mm Hg and was identified by means of gas-mass analysis, N.M.R. spectrometry and centesimal analysis.

EXAMPLE 10

Preparation of 2-(1',2'-dichloro-1',2'-difluoroethyl)-1,4-dioxan.

The synthesis was conducted by operating according to the modalities of example 1, using 238 g of 1,4-dioxan. 13 g of 2-(1',2'-dichloro-1',2'-difluoroethyl)-1,4-dioxan were obtained; the unreacted olefin was recovered by means of rectification. The product exhibited a boiling point of 115° at 50 mm of Hg and was identified by means of gas-mass analysis, N.M.R. spectrometry and centesimal analysis.

EXAMPLE 11

Preparation of 2-methyl-3,4-dichloro-3,4-difluoro-2-butanol

The product described in example 3 was prepared by using 36.5 g of dibenzoyl peroxide.

5.8 g of 2-methyl-3,4-dichloro-3,4-difluoro-2-butanol. were obtained.

EXAMPLE 12

Preparation of 2-methyl-3,4-dichloro-3,4-difluoro-2-butanol.

The product described in example 3 was prepared by using 45 g of 3,3,5-trimethyl-1,1-di-tert.butylperoxycyclohexane. Obtained were 17 g of 2-methyl-3,4-dichloro-3,4-difluoro-2-butanol.

EXAMPLE 13

Preparation of 2-(1',2'-dichloro-1',2'-difluoroethyl) tetrahydrofuran.

The product described in example 9 was prepared by using 36.5 g of dibenzoyl-peroxide. 18.4 g of 2-(1',2'-dichloro-1',2'-difluoroethyl) tetrahydrofuran were obtained.

EXAMPLE 14

Preparation of (1-methyl-2,3-dichloro-2,3-difluoropropyl) acetate.

The product described in example 6 was prepared by using 36.5 g of dibenzoylperoxide. 13 g of (1-methyl-2,3-dichloro-2,3-difluoropropyl) acetate were obtained.

What we claim is:

1. A process for preparing compounds having the formula:

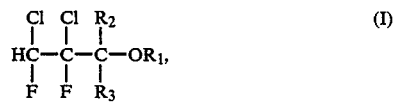

which are 1:1 adducts of 1,2-dichloro-difluoroethylene, and wherein:

$R_1$ = H, or alkyl or acyl containing from 1 to 10 carbon atoms, $R_2$, $R_3$, like or unlike each other, may be H, or an alkyl containing from 1 to 10 carbon atoms and where $R_1$ and $R_2$ may also form, together, an alkylene group containing from 2 to 10 carbon atoms, and from 0 to 2 oxygen atoms in the chain by means of an addition reaction induced by radicalic starters of 1,2-dichloro-difluoroethylene to alcohols, ethers and esters of the formula:

wherein:

$R_1$, $R_2$, $R_3$ are the same as defined hereinabove, and without at the same time forming any significant amounts of adducts having a ratio of 1,2-dichlorodifluoroethylene to said alcohols, ethers or esters higher than 1:1.

2. The process according to claim 1, in which peroxides are utilized as radicalic starters.

3. The process according to claim 2, in which it is operated with a molar ratio between olefine and ester, ether or alcohol, ranging from 100:1 to 1:100, and with a molar concentration of peroxide with respect to the olefin which is in the range of from 0.1 to 100%.

* * * * *